(12) United States Patent
Okuno et al.

(10) Patent No.: US 9,517,048 B2
(45) Date of Patent: Dec. 13, 2016

(54) ULTRASOUND ENDOSCOPE

(71) Applicant: OLYMPUS CORPORATION, Tokyo (JP)

(72) Inventors: Yoshiyuki Okuno, Fussa (JP);
Tomoyuki Hatakeyama, Hachioji (JP);
Katsuhiro Wakabayashi, Hachioji (JP);
Satoshi Yoshida, Kawagoe (JP);
Takanao Fujimura, Sagamihara (JP);
Teppei Tsuruta, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/131,248

(22) Filed: Apr. 18, 2016

(65) Prior Publication Data

US 2016/0228088 A1    Aug. 11, 2016

Related U.S. Application Data

(63) Continuation of application No. PCT/JP2015/061630, filed on Apr. 15, 2015.

(30) Foreign Application Priority Data

Jul. 14, 2014 (JP) .................. 2014-144280

(51) Int. Cl.
*A61B 8/14* (2006.01)
*A61B 8/12* (2006.01)
(Continued)

(52) U.S. Cl.
CPC .............. *A61B 8/12* (2013.01); *A61B 8/4483* (2013.01); *H04R 1/06* (2013.01); *H04R 3/00* (2013.01); *H04R 17/00* (2013.01)

(58) Field of Classification Search
CPC ......... A61B 8/12; A61B 8/4483; H04R 17/00; H04R 1/06; H04R 3/00
See application file for complete search history.

(56) References Cited

FOREIGN PATENT DOCUMENTS

| JP | H03-274899 A | 12/1991 |
|---|---|---|
| JP | H04-218765 A | 8/1992 |

(Continued)

OTHER PUBLICATIONS

International Search Report dated Jun. 23, 2015 issued in PCT/JP2015/061630.

(Continued)

*Primary Examiner* — Mark Remaly
(74) *Attorney, Agent, or Firm* — Scully, Scott, Murphy & Presser, P.C.

(57) ABSTRACT

An ultrasound endoscope, having a cable for connecting the ultrasound endoscope to a driving apparatus, includes an insertion section insertable into a subject, a plurality of transducers provided at a distal end portion, an electrode formed in each of the transducers, a wiring section connected to the electrode to electrically connect the electrode and the cable, and matching circuits, at least one of which is provided at an end of or partway in each of the wiring section. The electrode, the wiring section, and the matching circuits are provided in each of the plurality of transducers. The cable includes a core wire and an insulating layer enwrapping the core wire and functions as a matching section that matches electric impedance of each of the transducers between the plurality of transducers and the driving apparatus by varying a thickness or quality of material of the insulating layer.

9 Claims, 9 Drawing Sheets

(51) Int. Cl.
*H04R 1/06* (2006.01)
*H04R 3/00* (2006.01)
*H04R 17/00* (2006.01)
*A61B 8/00* (2006.01)

(56) References Cited

FOREIGN PATENT DOCUMENTS

| | | |
|---|---|---|
| JP | H10-192281 A | 7/1998 |
| JP | 2001-292496 A | 10/2001 |
| JP | 2003-135464 A | 5/2003 |
| JP | 2008-079909 A | 4/2008 |

OTHER PUBLICATIONS

Japanese Office Action dated Oct. 13, 2015 issued in JP 2015-544235.

ULTRASOUND ENDOSCOPE

CROSS REFERENCE TO RELATED APPLICATION

This application is a continuation application of PCT/JP2015/061630 filed on Apr. 15, 2015 and claims benefit of Japanese Application No. 2014-144280 filed in Japan on Jul. 14, 2014, the entire contents of which are incorporated herein by this reference.

BACKGROUND OF THE INVENTION

1. Field of the Invention

The present invention relates to an ultrasound endoscope including a transducer array including a plurality of transducers.

2. Description of the Related Art

In a field of diagnosis of an organism in a medical field and a field of non-destructive inspection of a machine structure, an ultrasound observation apparatus that observes an inside of a subject using ultrasound is used. The ultrasound observation apparatus includes a transducer that performs transmission of the ultrasound to the subject and reception of the ultrasound reflected by the subject. As the ultrasound observation apparatus, there is an ultrasound observation apparatus that includes a transducer array configured by arraying a plurality of transducers and performs scanning of an ultrasound beam.

A technique for providing, in an ultrasound observation apparatus, a matching circuit that performs matching of electric impedance between a transducer and a cable for signal input and output connected to the transducer and improving efficiency of transmission of a signal is described in, for example, Japanese Patent Application Laid-Open Publication No. 2003-135464 as a related art.

SUMMARY OF THE INVENTION

An ultrasound observation apparatus according to an aspect of the present invention is an ultrasound endoscope including a cable for connecting the ultrasound endoscope to a driving apparatus, the ultrasound endoscope including: an insertion section insertable into a subject; a distal end portion located at a distal end of the insertion section and including a curved surface in at least a part of a cylindrical surface shape; a plurality of transducers provided at the distal end portion and arrayed in a surface shape on the curved surface to configure one array surface; an electrode formed in each of the transducers; a wiring section connected to the electrode to electrically connect the electrode and the cable; and matching circuits, at least one of which is provided at an end of or partway in the wiring section, provided with an electric circuit including a capacitor or an inductor. The electrode, the wiring section, and the matching circuits are provided in each of the plurality of transducers. Concerning at least one of the matching circuits, the matching circuit is disposed in the distal end portion such that relative positions of the matching circuit and a transducer to which the matching circuit is connected are different from relative positions of another matching circuit and another transducer to which the other matching circuit is connected. The cable includes a core wire and an insulating layer enwrapping the core wire and functions as a matching section that matches electric impedance of each of the transducers between the plurality of transducers and the driving apparatus by varying a thickness or quality of material of the insulating layer.

DETAILED DESCRIPTION OF THE PREFERRED EMBODIMENTS

Preferred embodiments of the present invention are explained below with reference to the drawings. Note that, in respective figures used in the following explanation, scales are differentiated for each of components in order to show the respective components in sizes recognizable on the drawings. The present invention is not limited to only the numbers of the components, shapes of the components, ratios of sizes of the components, and relative positional relations among the respective components described in these figures.

First Embodiment

Figure 1:
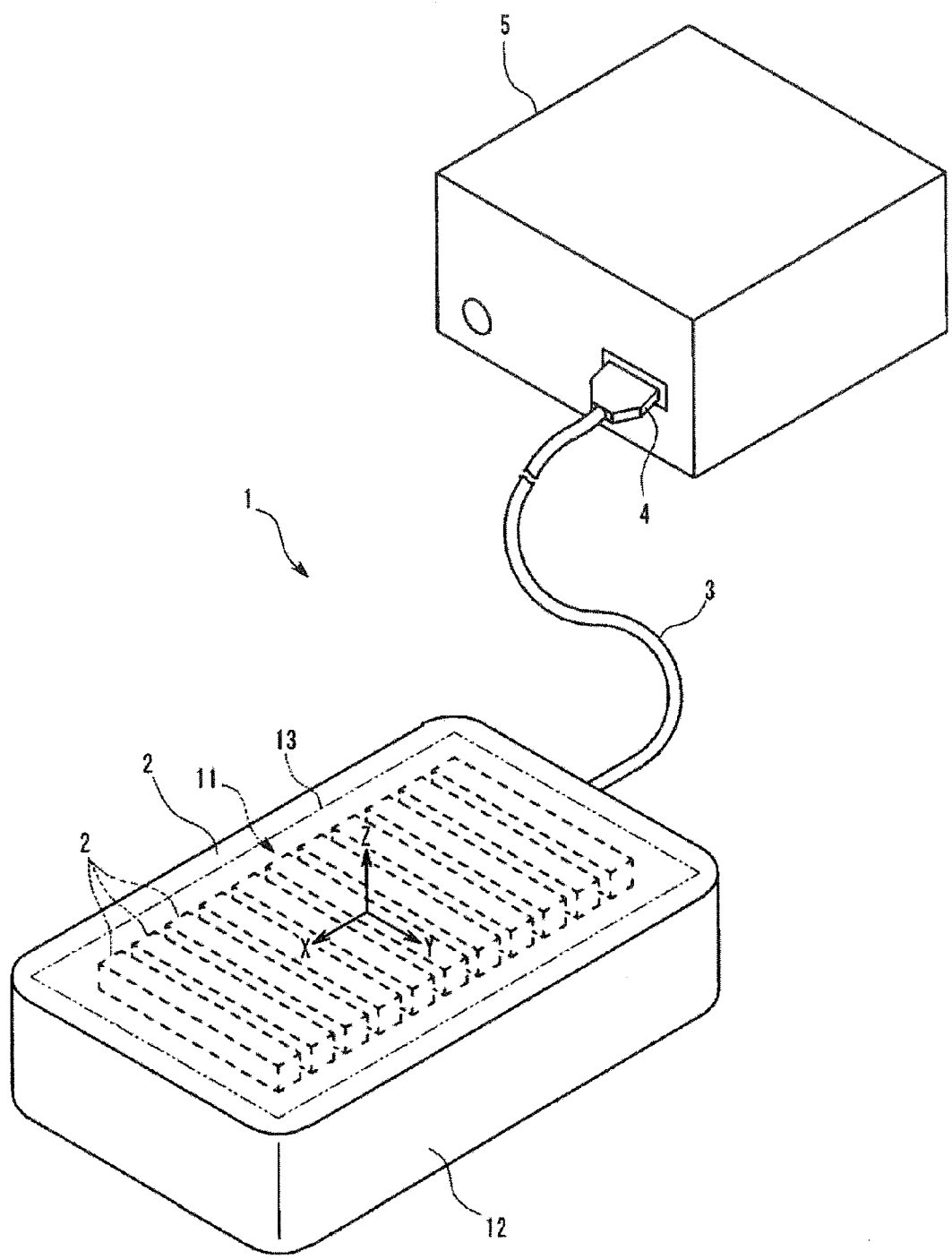
FIG. 1 is a perspective view of an ultrasound observation apparatus in a first embodiment.

An example of an embodiment of an ultrasound observation apparatus according to the present invention is explained below. An ultrasound observation apparatus 1 in the present embodiment shown in FIG. 1 is provided with an ultrasound transmitting/receiving section 2 and a connection cable 3 extending from the ultrasound transmitting/receiving section 2. The ultrasound observation apparatus 1 is electrically connected to a driving apparatus 5, which is an external apparatus, via a connector section 4 provided at an end portion of the connection cable 3.

The ultrasound observation apparatus 1 is schematically an apparatus that is driven by the driving apparatus 5 and electronically scans an ultrasound beam on a subject to thereby obtain an ultrasound tomographic image (a B mode image) of the subject. A not-shown display apparatus or the like for displaying the ultrasound tomographic image is connected to the driving apparatus 5. Note that the ultrasound observation apparatus 1 may adopt a form for performing scanning of the ultrasound beam inside the subject or may adopt a form for performing the scanning of the ultrasound beam outside the subject.

The ultrasound transmitting/receiving section 2 includes a transducer array 11 configured by arraying a plurality of transducers 10 and a housing section 12 that houses the transducer array 11. In the transducer array 11, the plurality of transducers 10 are arrayed along an array surface 13, which is a plane or a curved surface.

The transducer 10 is not particularly limited as long as the transducer 10 is capable of converting an electric signal and ultrasound to each other. However, for example, a piezoelectric element or an electrostrictive element such as piezoelectric ceramics or an ultrasound transducer (MUT: micromachined ultrasonic transducer) by a micromachine technology can be applied. In the present embodiment, as an example, the transducer 10 is a piezoelectric element.

The number and a form of an array of the plurality of transducers 10 configuring the transducer array 11 are not particularly limited. The transducer array 11 may be a one-dimensional array (1D array) configured by arraying the plurality of transducers 10 in one row along the array surface 13 or may be a two-dimensional array (2D array) configured by arraying the plurality of transducers 10 in a matrix shape along the array surface 13. When the transducer array 11 is the two-dimensional array, the form of the array of the plurality of transducers 10 on the array surface 13 is not limited to the matrix shape and may be a zigzag shape.

As a form of a piezoelectric element array configured by arraying the plurality of transducers 10 in a matrix shape along the array surface 13, a configuration generally called 1.25D array in which a width of an ultrasound beam is variable and a configuration generally called 1.5D array in which a width of an ultrasound beam and a focal length are variable are known. The transducer array 11 may adopt such forms called 1.25D array and 1.5D array.

A shape of the array surface 13 is not particularly limited and may be a plane or may be a curved surface such as a cylindrical surface or a spherical surface. The array surface 13 may have a shape, a curvature of which changes partway.

In the present embodiment, as an example, in the transducer array 11, the plurality of transducers 10 are arrayed in one row along the array surface 13, which is a plane. In the following explanation, an axis extending along an array direction of the plurality of transducers 10 on the array surface 13 is referred to as X axis and an axis orthogonal to the X axis on the array surface 13 is referred to as Y axis. An axis orthogonal to the array surface 13 is referred to as Z axis.

In the present embodiment, the individual transducer 10 has a shape elongated in the Y-axis direction orthogonal to the array direction (the X-axis direction) when viewed from the Z-axis direction.

Figure 2:
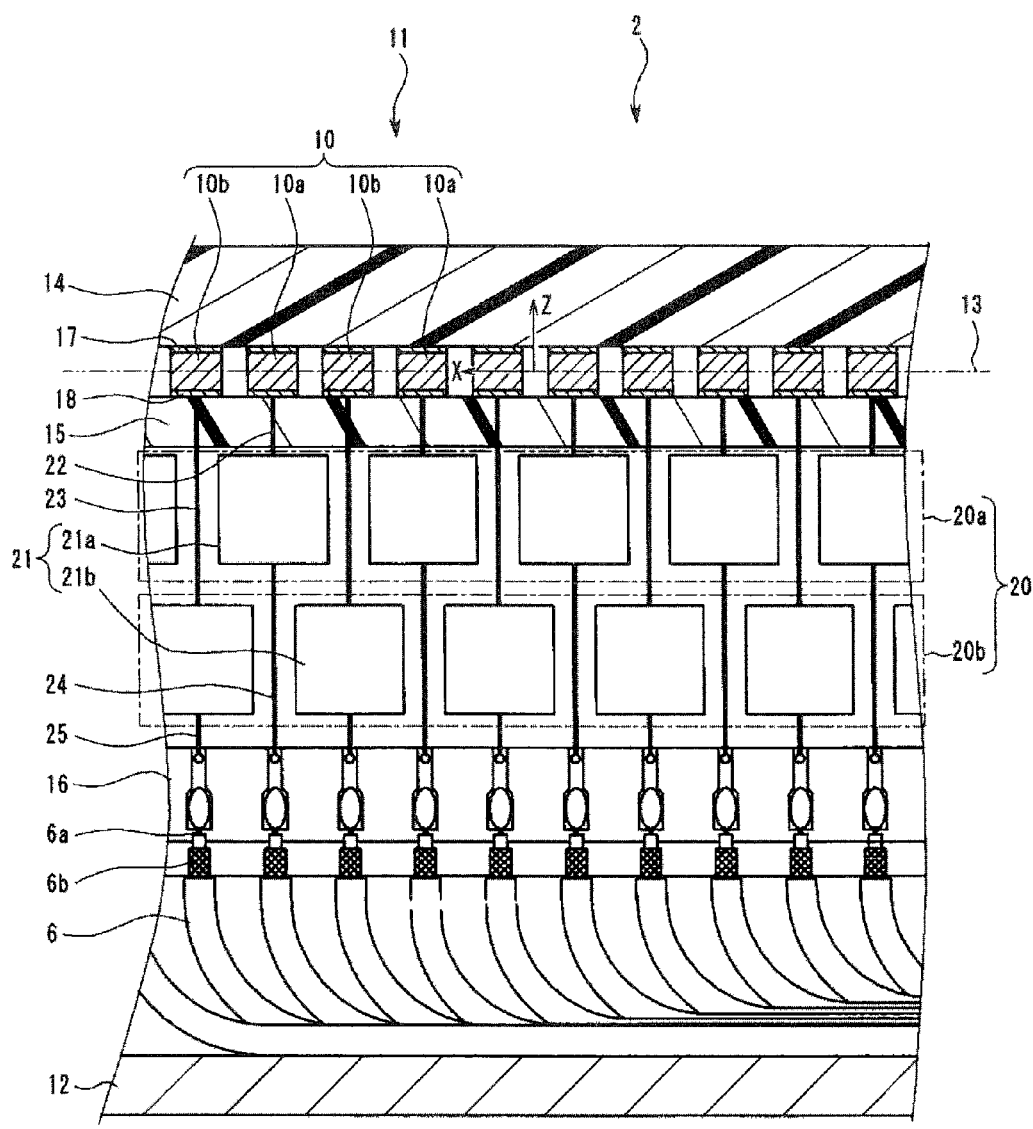
FIG. 2 is a sectional view of an ultrasound transmitting/receiving section in the first embodiment.
Figure 3:
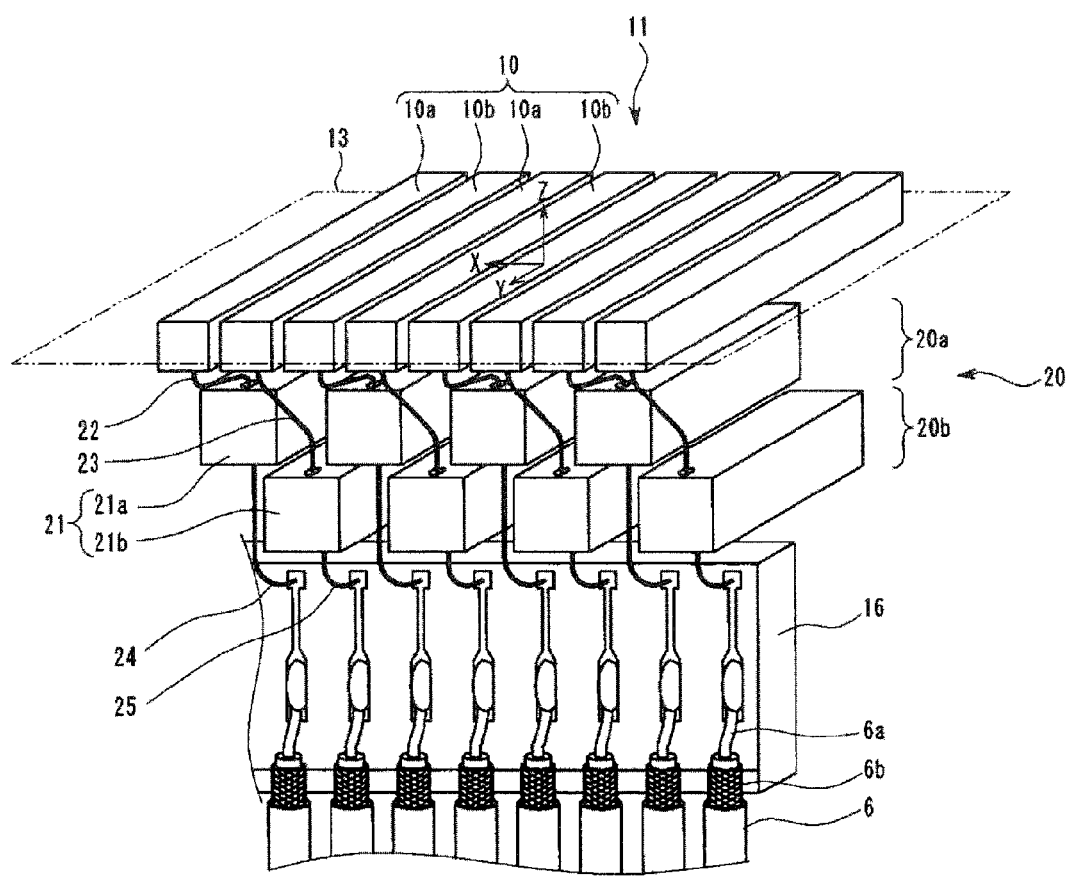
FIG. 3 is a perspective view for explaining disposition of transducers and matching circuits in the ultrasound transmitting/receiving section in the first embodiment.
Figure 4:
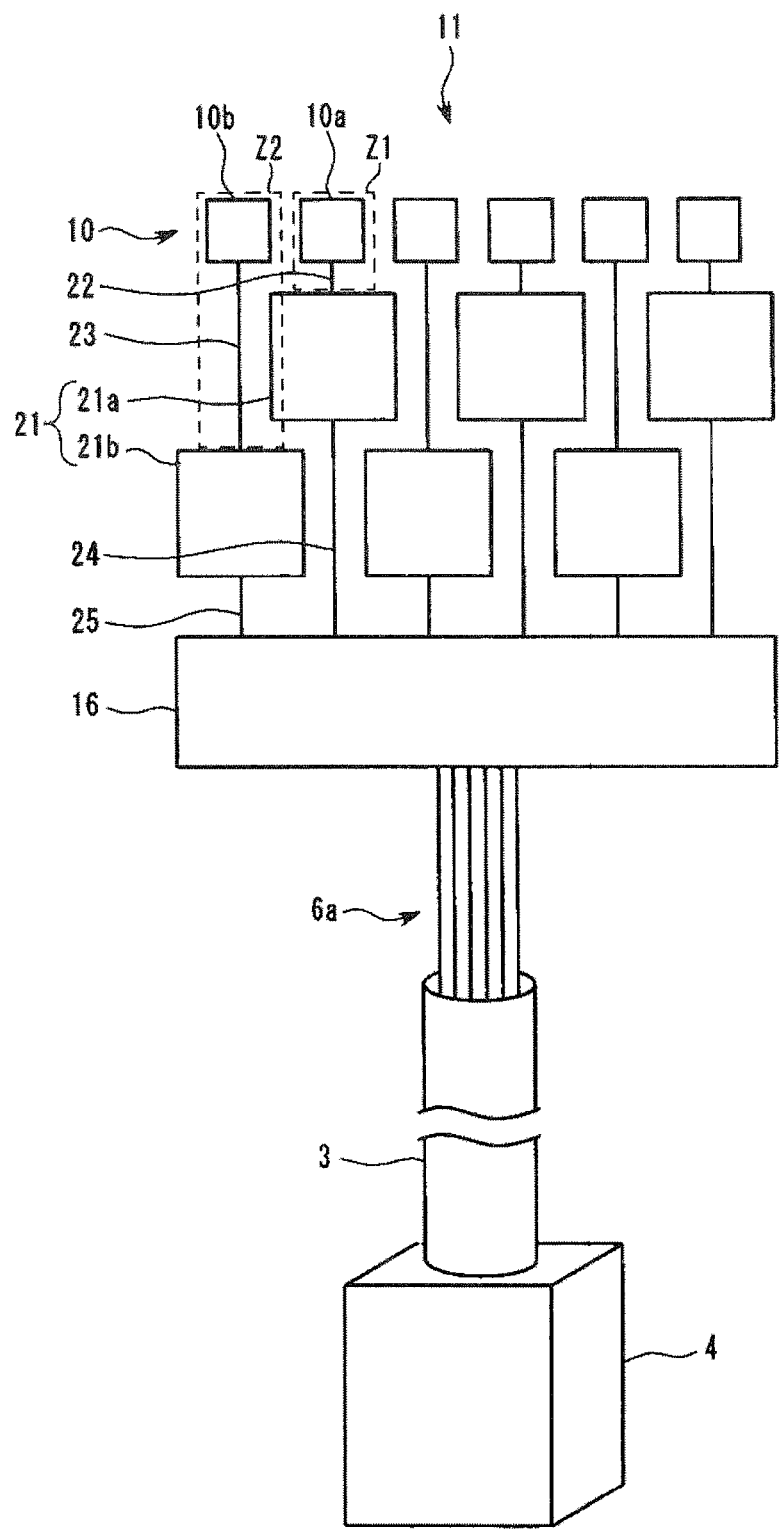
FIG. 4 is a schematic diagram showing electric connection of the transducers, the matching circuits, and a circuit board in the first embodiment.

FIG. 2 is a sectional view of an X-Z plane of the ultrasound transmitting/receiving section 2. FIG. 3 is a perspective view for explaining disposition of the transducers 10 and matching circuits 21. FIG. 4 is a schematic diagram showing electric connection of the transducers 10, the matching circuits 21, and core wires 6a of coaxial cables 6. As shown in FIG. 2, the ultrasound transmitting/receiving section 2 is provided with the transducers 10 and an electric matching section 20.

The transducer 10 includes an upper electrode 17 and a lower electrode 18. The upper electrode 17 is electrically connected to a not-shown electric wire inserted through a connection cable 3. The upper electrode 17 is grounded in a state in which a connector section 4 is connected to the driving apparatus 5.

As explained in detail below, the lower electrode 18 is electrically connected to, via a wiring section and the matching circuit 21, the core wire 6a of the coaxial cable 6 inserted through the connection cable 3. In a state in which the connector section 4 is connected to the driving apparatus 5, the lower electrode 18 is electrically connected to an input/output circuit for an electric signal of the driving apparatus 5. That is, the lower electrode 18 is an electrode for input and output of a signal. Note that, in the transducer 10, the upper electrode 17 is an electrode for input and output of a signal and the lower electrode 18 may be an electrode set to ground potential.

In the following explanation, in a direction along an axis orthogonal to the array surface 13 of the transducer array 11, a transmitting direction of an ultrasound beam is referred to as front and a direction opposite to the direction is referred to as back. That is, a direction extending from an inner side to an outer side of the ultrasound transmitting/receiving section 2 along the axis orthogonal to the array surface 13 of the transducer array 11 is the front. In the present embodiment in which the array surface 13 has a planar shape, the axis orthogonal to the array surface 13 is the Z axis. Note that, when the array surface 13 is a curved surface, a direction of the axis orthogonal to the array surface 13 changes according to a position of the transducer 10.

The transducer 10 is disposed such that the upper electrode 17 faces the front and the lower electrode 18 faces the back. In other words, the upper electrode 17 is provided on a front end face (a vibration surface) of the transducer 10 and the lower electrode 18 is provided on a rear end face (a rear surface) of the transducer 10.

The housing section 12 that houses the transducer array 11 opens toward the front. In the present embodiment, as an example, an acoustic matching layer 14 is disposed in the front of the transducer array 11. The acoustic matching layer 14 is a member that performs acoustic impedance matching between the transducer 10 and a subject. When the acoustic impedance matching is unnecessary between the transducer 10 and the subject, the acoustic matching layer 14 is not disposed. An acoustic lens that performs formation of an ultrasound beam may be disposed in the front of the acoustic matching layer 14.

A backing material 15 is disposed in the back of the transducer 10. The backing material 15 is a member that absorbs ultrasound radiated toward the back from the transducer 10 and unnecessary ultrasound such as ultrasound made incident on the transducer 10 from the back.

The electric matching section 20 is disposed in the back of the transducer 10. The electric matching section 20 is configured to perform electric impedance matching between the transducer 10 and the core wire 6a of the coaxial cable 6. Note that, in the present embodiment shown in the figures, the electric matching section 20 is disposed further in the back than the backing material 15. However, a part or all of the electric matching section 20 is embedded in the backing 15.

The electric matching section 20 is provided with a plurality of matching circuits 21 electrically connected respectively to the lower electrodes 18 of the plurality of transducers 10. The matching circuit 21 is provided at an end of or partway in a wiring section that electrically connects the lower electrode 18 of the transducer 10 and the core wire 6a of the coaxial cable 6. In the present embodiment, as an example, the matching circuit 21 is provided partway in the wiring section. Explanation of a configuration of the matching circuit 21 is omitted because the configuration is publicly known. However, the matching circuit 21 is provided with an electric circuit including, for example, a capacitor or an inductor.

In the present embodiment, as an example, the matching circuit 21 and the core wire 6a of the coaxial cable 6 is electrically connected via a circuit board 16 disposed near the electric matching section 20. A shield wire 6b of the coaxial cable 6 is connected to the ground potential. Note that the circuit board 16 may be divided into a plurality of circuit boards.

Details of a configuration of the electric matching section 20 are explained below. The plurality of matching circuits 21 provided in the electric matching section 20 are disposed in the back of the transducers 10, to which the matching circuits 21 are respectively connected, in positions where a part of front end faces are opposed to a part of rear end faces of the transducers 10.

The plurality of matching circuits 21 in the present embodiment are arrayed in the same way as that of the array of the plurality of transducers 10 when viewed from the direction orthogonal to the array surface 13 (e.g., the front). However, the plurality of matching circuits 21 are disposed to be divided into a plurality of layers in a front-back direction when viewed from a direction parallel to the array surface 13 (a side). In other words, when viewed from the direction orthogonal to the array surface 13, the plurality of matching circuits 21 are disposed in positions overlapping the transducers 10 to which the plurality of matching circuits 21 are respectively connected. The plurality of matching circuits 21 are disposed to be divided into a plurality of layers having different distances from the array surface 13 along the array surface 13. The respective plurality of layers have predetermined thickness in the front-back direction and do not cross one another.

The matching circuits 21 connected to the transducers 10 adjacent to each other in the transducer array 11 are disposed to be included in the different layers. The matching circuits 21 connected to the transducers 10 adjacent to each other and included in different layers have sizes partially overlapping each other when viewed from the direction orthogonal to the array surface 13. That is, in the present embodiment, when a certain one matching circuit 21 is focused on, relative positions of the matching circuit 21 and the transducer 10 connected to the matching circuit 21 are different from relative positions of the other matching circuits 21 and the other transducers 10 connected to the other matching circuits 21.

In the present embodiment, as an example, the electric matching section 20 includes an upper layer 20a and a lower layer 20b divided in the front-back direction. That is, the upper layer 20a is a layer close to the array surface 13. The lower layer 20b is a layer further apart from the array surface 13 than the upper layer 20a.

As shown in FIG. 2 and FIG. 3, the plurality of matching circuits 21 are divided into a group consisting of first matching circuits 21a disposed in the upper layer 20a and a group consisting of second matching circuits 21b disposed in the lower layer 20b. That is, in the present embodiment, when a certain one matching circuit 21 is focused on, a distance between a center of the matching circuit 21 and a center of the transducer 10 connected to the matching circuit 21 differs from distances between centers of the other matching circuits 21 and centers of the other transducers 10 connected to the other matching circuits 21. In the present embodiment, as an example, the first matching circuit 21a and the second matching circuit 21b have the same impedance.

The transducer 10 connected to the first matching circuit 21a via a first connection line 22 is referred to as first transducer 10a. The transducer 10 connected to the second matching circuit 21b via a second connection line 23 is referred to as second transducer 10b. Therefore, the first matching circuit 21a is disposed in the back of the first transducer 10a in a position where a part of a front end face is opposed to a part of a rear end face of the first transducer 10a. The second matching circuit 21b is disposed in the back of the second transducer 10b in a position where a part of a front end face is opposed to a part of a rear end face of the second transducer 10b.

As in the present embodiment, when the plurality of transducers 10 are arrayed in one row, the first transducer 10a and the second transducer 10b are alternately disposed in the array direction. When the transducer array 11 is a form in which the plurality of transducers 10 are arrayed in a matrix shape, the first transducers 10a and the second transducers 10b are alternately disposed along a row direction and a column direction in a chessboard shape (a checkered shape). That is, the first transducers 10a are not adjacent to one another in the array direction. Similarly, the second transducers 10b are not adjacent to one another in the array direction.

The first matching circuit 21a and the second matching circuit 21b respectively connected to the first transducer 10a and the second transducer 10b, which are a pair of transducers adjacent to each other, have sizes partially overlapping each other when viewed from the front, which is the direction orthogonal to the array surface 13.

As explained above, in the present embodiment, the second matching circuit 21b is disposed in the back of the first matching circuit 21a in a position where a part of a frontend face is opposed to a part of a rear end face of the first matching circuit 21a. Note that the second matching circuit 21b may be disposed in a position where a part of the front end face is opposed to a part of a rear end face of the first transducer 10b.

In the present embodiment, the plurality of transducers 10 are arrayed in one row along the X axis. Therefore, the plurality of matching circuits 21 disposed below the respective transducers 10 are seen as being arrayed in one row along the X axis when viewed from the front along the Z axis. On the other hand, as shown in FIG. 2, in a cross section by an X-Z plane, the matching circuits 21 adjacent to each other are disposed in layers, distances to which from the array surface 13 are different. Therefore, the matching circuits 21 are disposed in a zigzag shape in two rows in a direction along the X axis.

By allocating the plurality of matching circuits 21 to the upper layer 20a and the lower layer 20b, distances to which from the array surface 13 are different, in this way, an inter-center distance of an array of the matching circuits 21 viewed from the direction orthogonal to the array surface 13 can be set shorter than an external shape of the matching circuit 21. Consequently, an inter-center distance of an array of the transducers 10 can be reduced without being affected by an external shape dimension of the matching circuit 21.

The first matching circuit 21a is electrically connected to the lower electrode 18 of the first transducer 10a via the first connection line 22 extended from the rear end face of the first transducer 10a. The first matching circuit 21a is electrically connected to the circuit board 16 via a first cable 24 extended from the rear end face of the first matching circuit 21a. The first matching circuit 21a is electrically connected to the core wire 6a of the coaxial cable 6 via the first cable 24 and the circuit board 16.

The second matching circuit 21b is electrically connected to the lower electrode 18 of the second transducer 10b via the second connection line 23 extended from the rear end face of the second transducer 10*b*. The second matching circuit 21*b* is electrically connected to the circuit board 16 via a second cable 25 extended from the rear end face of the second matching circuit 21*b*. The second matching circuit 21*b* is electrically connected to the core wire 6*a* of the coaxial cable 6 via the second cable 25 and the circuit board 16.

In the present embodiment, the first matching circuit 21*a* and the second matching circuit 21*b* are disposed in positions, distances to which from the array surface 13 are different. Therefore, a length of the first connection line 22 for connecting the transducer 10 and the first matching circuit 21*a* and a length of the second connection line 23 for connecting the transducer 10 and the second matching circuit 21*b* are different. More specifically, the second connection line 23 is longer than the first connection line 22 by thickness of the upper layer 20*a*. Therefore, first impedance Z1 of the transducer 10 and the first connection line 22 and second impedance Z2 of the transducer 10 and the second connection line 23 are different. The second impedance Z2 is higher than the first impedance Z1.

Therefore, in the present embodiment, as schematically shown in FIG. 4, the first cable 24 is formed longer than the second cable 25 such that a total length of the first connection line 22 and the first cable 24 is the same as a total length of the second connection line 23 and the second cable 25.

In this way, in the present embodiment, the difference between the first impedance Z1 and the second impedance Z2 caused by disposing the first matching circuit 21*a* and the second matching circuit 21*b* in the positions, the distances to which from the transducer 10 are different, is eliminated by differentiating the length of the first cable 24 connected to the first matching circuit 21*a* and the length of the second cable 25 connected to the second matching circuit 21*b*.

Therefore, in the present embodiment, when the connector section 4 is connected to the driving apparatus 5, it is possible to equally perform impedance matching between all the transducers 10 configuring the transducer array 11 and the driving apparatus 5. It is possible to improve efficiency of transmission of a signal.

As explained above, in the ultrasound observation apparatus 1 in the present embodiment, a reduction in size and improvement of resolution are realized by reducing the inter-center distance of the array of the transducers 10 in the transducer array 11 and improvement of sensitivity is realized by improving efficiency of transmission of a signal between the transducer 10 and the driving apparatus 5.

Note that, in the present embodiment, the first matching circuit 21*a* and the second matching circuit 21*b* are explained as having the same impedance. However, the first matching circuit 21*a* and the second matching circuit 21*b* may have different impedances. A plurality of matching circuits belonging to the first matching circuits 21*a* or the second matching circuit 21*b* may respectively have different impedances. For example, by differentiating the impedances of the respective matching circuits, it is possible to perform impedance matching according to a difference in characteristics of the transducers 10 respectively connected to the matching circuits.

Figure 5:
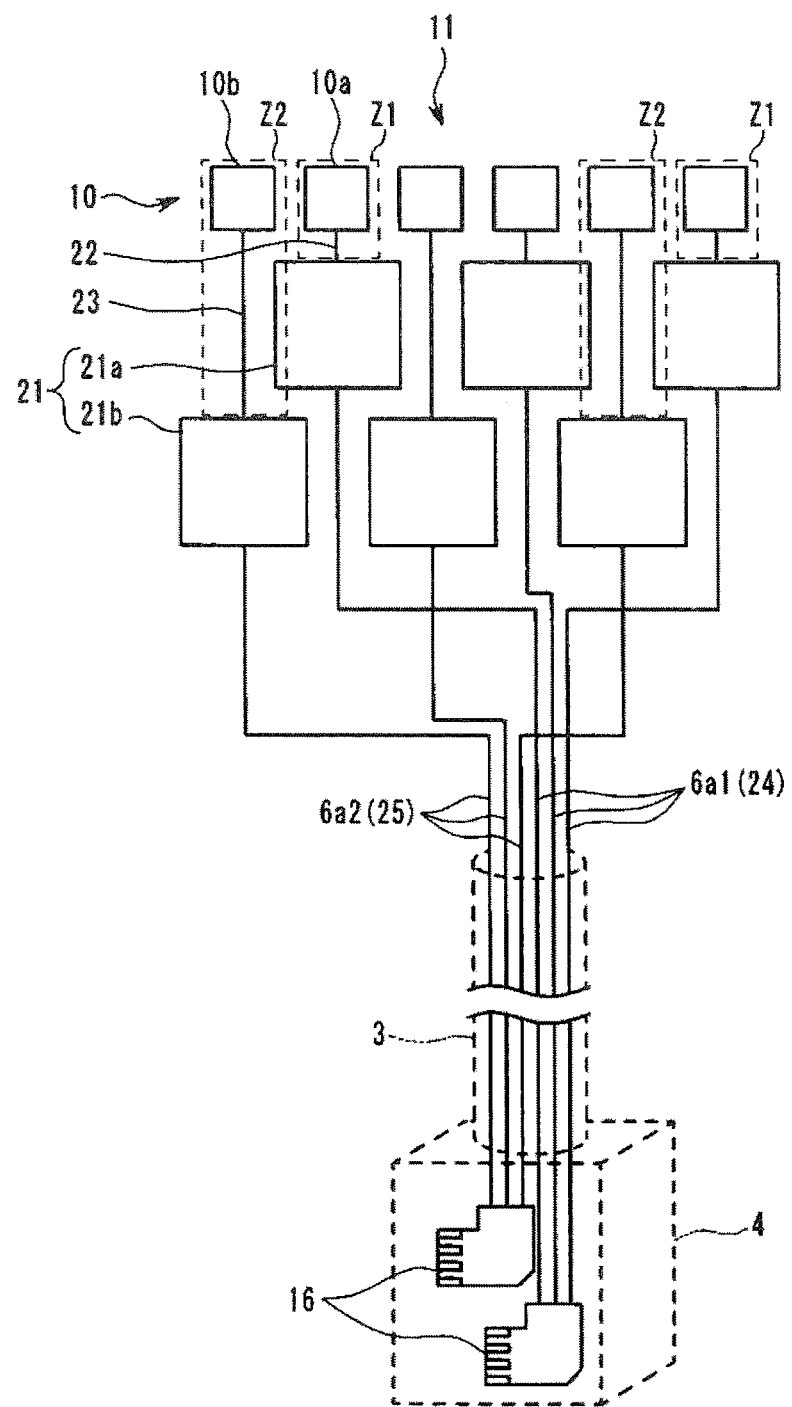
FIG. 5 is a schematic diagram showing electric connection of the transducers, the matching circuits, and the circuit board in a modification of the first embodiment.

A modification of the present embodiment is explained with reference to FIG. 5. In the present embodiment explained above, the circuit board 16 is disposed in the ultrasound transmitting/receiving section 2. However, the circuit board 16 may be disposed in the connector section 4 as in the modification shown in FIG. 5.

That is, in this modification, the matching circuit 21 and the circuit board 16 are electrically connected via the core wire 6*a* of the coaxial cable 6. In this modification, a length of a first core wire 6*a*1 for electrically connecting the first matching circuit 21*a* and the circuit board 16 and a length of a second core wire 6*a*2 for electrically connecting the second matching circuit 21*b* and the circuit board 16 are differentiated. The first core wire 6*a*1 is equivalent to the first cable 24 in the embodiment explained above. The second core wire 6*a*2 is equivalent to the second cable 25 in the embodiment explained above.

More specifically, the first core wire 6*a*1 is formed longer than the second core wire 6*a*2 such that a total length of the first connection line 22 and the first core wire 6*a*1 is the same as a total length of the second connection line 23 and the second core wire 6*a*2. As a method of forming the first core wire 6*a*1 longer than the second core wire 6*a*2, as illustrated in FIG. 5, a method of disposing the circuit board 16, to which the first core wires 6*a*1 is connected, in a position farther than the circuit board 16, to which the second core wire 6*a*2 is connected, is conceivable.

As in the embodiment explained above, in this modification, when the connector section 4 is connected to the driving apparatus 5, it is possible to equally perform impedance matching between all the transducers 10 configuring the transducer array 11 and the driving apparatus 5. It is possible to improve efficiency of transmission of a signal.

Therefore, in the ultrasound observation apparatus 1 in this modification, a reduction in size and improvement of resolution are realized by reducing the inter-center distance of the array of the transducers 10 in the transducer array 11 and improvement of sensitivity is realized by improving efficiency of transmission of a signal between the transducer 10 and the driving apparatus 5.

Note that, in the present modification, by differentiating lengths of the first core wire 6*a*1 and the second core wire 6*a*2 from the matching circuit 21 to the circuit board 16, a difference in impedance is caused between the first core wire 6*a*1 and the second core wire 6*a*2. However, a method of causing a difference in impedance between the first core wire 6*a*1 and the second core wire 6*a*2 is not limited to this.

For example, by differentiating thickness and/or a material of an insulating layer interposed between the core wire 6*a* and the shield wire 6*b*, it is possible to cause a difference in impedance of the core wire 6*a* of the coaxial cable 6. A coaxial cable having a thinner insulating layer has higher impedance even if a length is the same. A coaxial cable including an insulating layer having lower insulation has higher impedance even if a length is the same.

As explained above, in the ultrasound observation apparatus 1 in the present embodiment, concerning at least one of the wiring sections, the matching circuits, and the cables, by using the wiring section, the matching circuit, or the cable having different electric impedance, electric impedance for each of the transducers 10 between the plurality of transducers 10 and the driving apparatus is adjusted.

Second Embodiment

A second embodiment of the present invention is explained below. In the following explanation, only differences from the first embodiment are explained. The same components as the components in the first embodiment are denoted by the same reference numerals and signs. Explanation of the components is omitted as appropriate.

Figure 6:
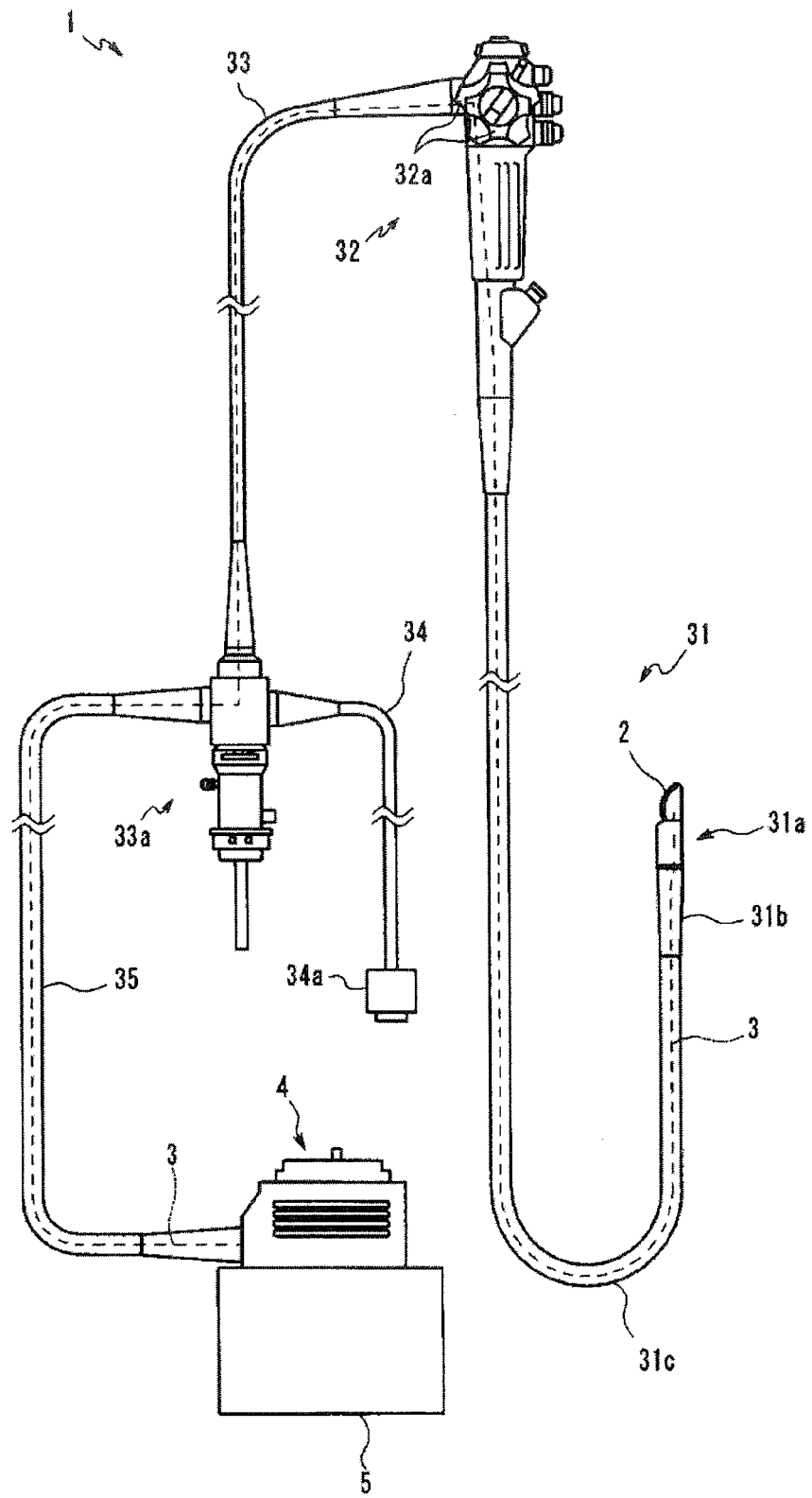
FIG. 6 is a diagram showing an exterior of an ultrasound observation apparatus in a second embodiment.

The ultrasound observation apparatus 1 in the present embodiment shown in FIG. 6 has a form of an ultrasound endoscope. Note that a form of the ultrasound observation apparatus 1 is not limited to the ultrasound endoscope and may be a form called ultrasound probe introduced into a subject via a conduit of an endoscope.

Detailed explanation of an entire configuration of the ultrasound endoscope is omitted because the configuration is well known. A schematic configuration of the ultrasound observation apparatus 1 is explained below. The ultrasound observation apparatus 1 mainly includes an insertion section 31 insertable into a body of a subject, an operation section 32 located at a proximal end of the insertion section 31, and a universal cord 33 extending from a side of the operation section 32.

The insertion section 31 is configured by concatenating a distal end portion 31a disposed at a distal end, a bendable bending section 31b disposed on a proximal end side of the distal end portion 31a, and a flexible tube section 31c having flexibility disposed on a proximal end side of the bending section 31b and connected to a distal end side of the operation section 32. Note that the ultrasound observation apparatus 1 may be an ultrasound observation apparatus of a form of a so-called rigid endoscope not including a part having flexibility in the insertion section 31.

At the distal end portion 31a of the insertion section 31, besides the ultrasound transmitting/receiving section 2, although not shown in the figure, an image pickup apparatus and a lighting apparatus for picking up an optical image, a treatment instrument insert-through port for projecting a treatment instrument, and the like are provided.

In the operation section 32, an angle operation knob 32a for operating bending of the bending section 31b is provided. In the operation section 32, a switch and the like for performing control of a delivery operation and a suction operation of fluid from an opening section provided at the distal end portion 31a are provided.

An endoscope connector 33a connected to a not-shown light source apparatus is provided in a proximal end portion of the universal cord 33. Light emitted from the light source apparatus is transmitted through the universal cord 33 and an optical fiber cable inserted through the operation section 32 and the insertion section 31 and emitted from the lighting apparatus disposed at the distal end portion 31a. Note that the ultrasound observation apparatus 1 may be a configuration in which a light source apparatus such as an LED is provided in the lighting apparatus disposed at the distal end portion 31a.

An electric cable 34 and an ultrasound cable 35 extend from the endoscope connector 33a. The electric cable 34 is detachably connected to a not-shown camera control unit via an electric connector 34a. The camera control unit is an apparatus that outputs an image picked up by the image pickup apparatus provided at the distal end portion 31a to a not-shown image display apparatus.

The ultrasound cable 35 is detachably connected to the driving apparatus 5 via the connector section 4. The connection cable 3 extending from the ultrasound transmitting/receiving section 2 is connected to the connector section 4 through the insertion section 31, the operation section 32, the universal cord 33, and the ultrasound cable 35.

Figure 7:
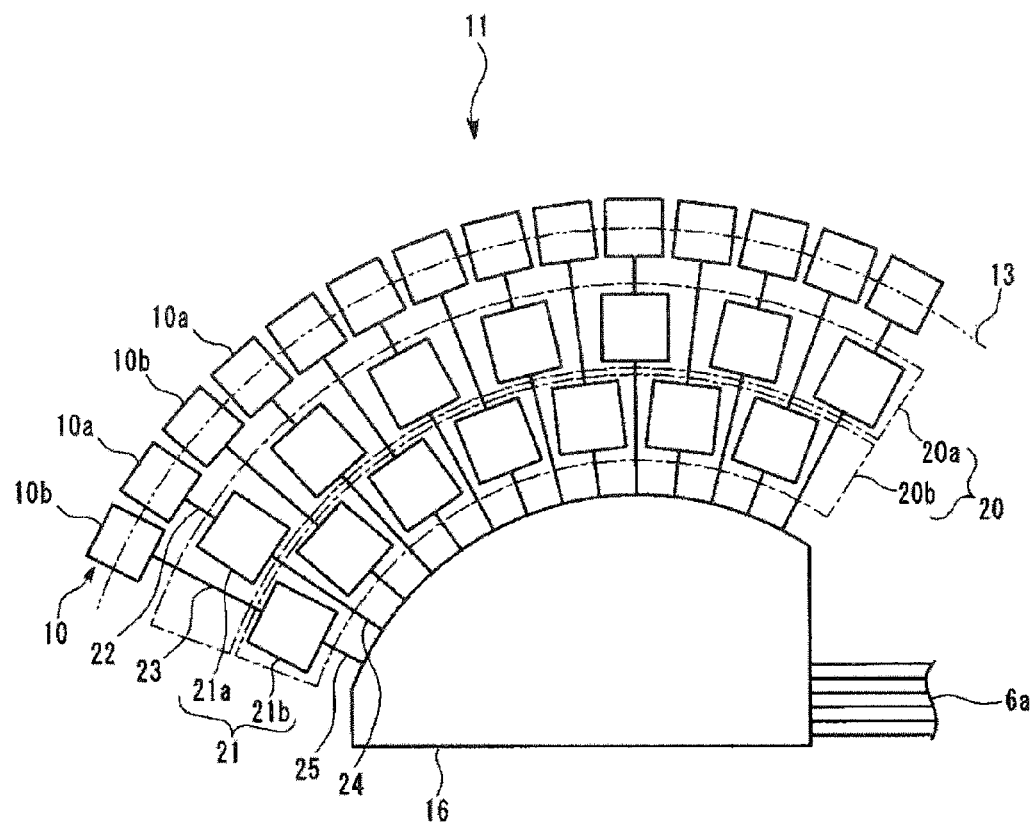
FIG. 7 is a diagram for explaining disposition of transducers and matching circuits in an ultrasound transmitting/receiving section in the second embodiment.

As shown in FIG. 7, the ultrasound transmitting/receiving section 2 in the present embodiment is provided with the transducer array 11 configured by arraying the plurality of transducers 10 in a circumferential direction along the array surface 13, which is a curved surface having a cylindrical surface shape. The ultrasound transmitting/receiving section 2 in the present embodiment is capable of performing so-called electronic convex scanning for performing scanning of an ultrasound beam in a substantially arcuate shape.

In the present embodiment, as in the first embodiment, the electric matching section 20 is disposed in the back of the transducer array 11. The electric matching section 20 includes the plurality of matching circuits 21 respectively connected to the plurality of transducers 10. The matching circuits 21 connected to the transducers 10 adjacent to each other in the transducer array 11 are disposed in positions, distances to which from the array surface 13 are different, not to overlap when viewed from the direction parallel to the array surface 13.

The first matching circuit 21a disposed in the upper layer 20a close to the array surface 13 is connected to the first transducer 10a via the short first connection line 22. The second matching circuit 21b disposed in the lower layer 20b farther than the upper layer 20a from the array surface 13 is connected to the second transducer 10b via the second connection line 23 longer than the first connection line 22.

The first matching circuit 21a is connected to the circuit board 16 via the first cable 24. The second matching circuit 21b is connected to the circuit board 16 via the second cable 25.

The first cable 24 is formed longer than the second cable 25 such that a total length of the first connection line 22 and the first cable 24 is the same as a total length of the second connection line 23 and the second cable 25.

In the present embodiment having the configuration explained above, as in the first embodiment, by allocating the plurality of matching circuits 21 to the upper layer 20a and the lower layer 20b, distances to which from the array surface 13 are different, an inter-center distance of an array of the matching circuits 21 viewed from the direction orthogonal to the array surface 13 can be set shorter than an external shape of the matching circuit 21. Consequently, an inter-center distance of an array of the transducers 10 can be reduced without being affected by an external shape dimension of the matching circuit 21.

In the present embodiment, as in the first embodiment, the difference between the first impedance Z1 and the second impedance Z2 caused by disposing the first matching circuit 21a and the second matching circuit 21b in the positions, the distances to which from the transducer 10 are different, is eliminated by differentiating the length of the first cable 24 connected to the first matching circuit 21a and the length of the second cable 25 connected to the second matching circuit 21b. Therefore, in the present embodiment, when the connector section 4 is connected to the driving apparatus 5, it is possible to equally perform impedance matching between all the transducers 10 configuring the transducer array 11 and the driving apparatus 5. It is possible to improve efficiency of transmission of a signal.

As explained above, in the ultrasound observation apparatus 1 in the present invention, a reduction in size and improvement of resolution are realized by reducing the inter-center distance of the array of the transducers 10 in the transducer array 11 and improvement of sensitivity is realized by improving efficiency of transmission of a signal between the transducer 10 and the driving apparatus 5.

Note that, in the present embodiment, the transducer array 11 is configured by arraying the plurality of transducers 10 in a part in a circumferential direction of the array surface 13 having a cylindrical surface shape. However, the transducer array 11 may be configured by arraying the plurality of transducers 10 in the entire circumferential direction of the array surface 13 having the cylindrical surface shape. A form including the transducer array 11 configured by arraying the plurality of transducers 10 in the entire circumferential direction in this way is called electronic radial scanning system.

Third Embodiment

Figure 8:
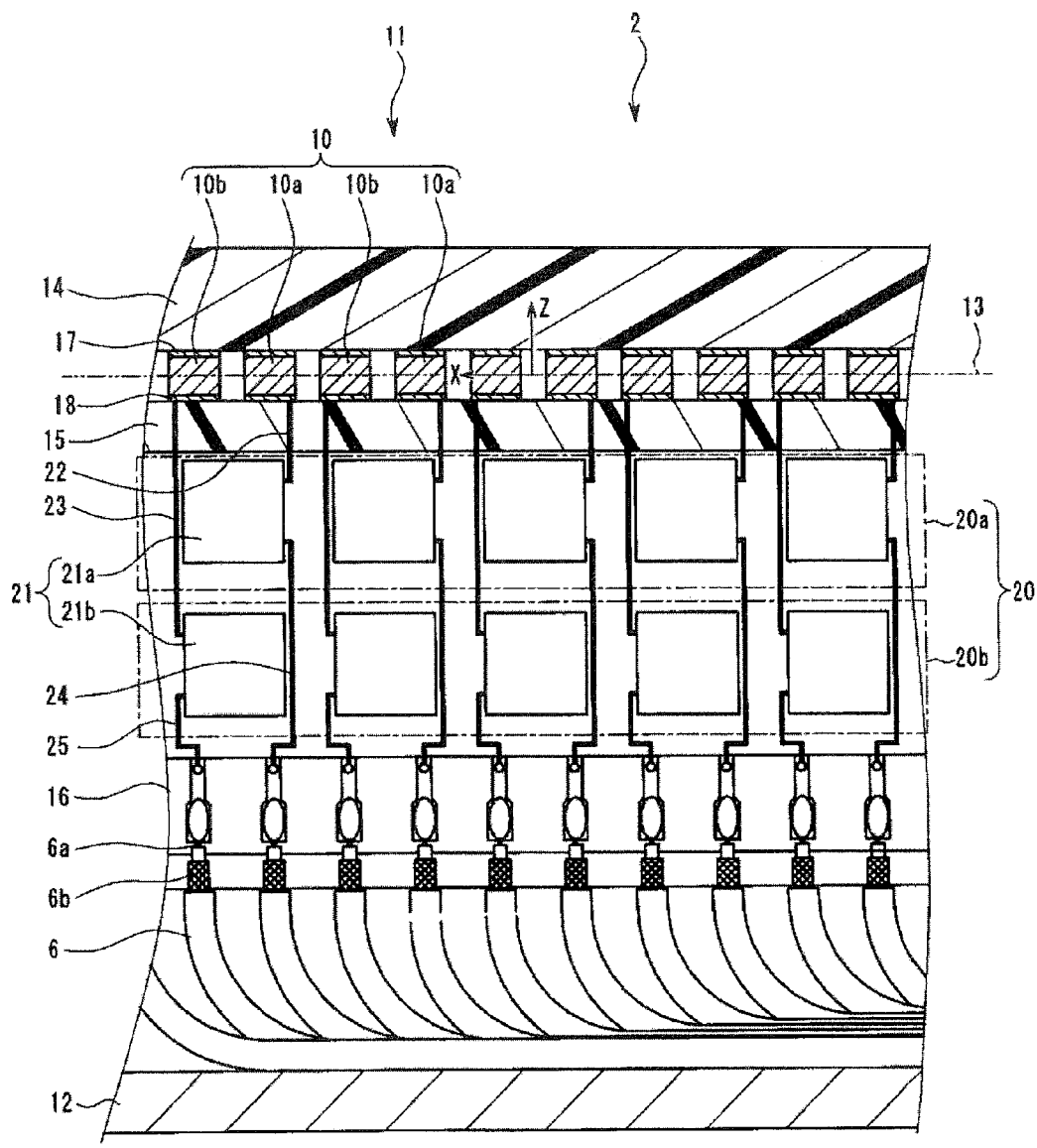
FIG. 8 is a sectional view of an ultrasound transmitting/receiving section in a third embodiment.

A third embodiment of the present invention is explained below. In the following explanation, only differences from the first embodiment are explained. The same components as the components in the first embodiment are denoted by the same reference numerals and signs. Explanation of the components is omitted as appropriate. The ultrasound observation apparatus 1 in the present embodiment shown in FIG. 8 differs from the first and second embodiments in a form of an array of the plurality of matching circuits 21.

The ultrasound observation apparatus 1 in the present embodiment is the same as the first and second embodiments in that the plurality of matching circuits 21 are divided into a group consisting of first matching circuits 21a disposed in the upper layer 20a and a group consisting of second matching circuits 21b disposed in the lower layer 20b. However, in the present embodiment, the first matching circuit 21a and the second matching circuit 21b respectively connected to the first transducer 10a and the second transducer 10b, which are a pair of transducers adjacent to each other, are disposed to entirely overlap when viewed from the front, which is the direction orthogonal to the array surface 13. That is, when viewed from the front, the second matching circuit 21b is disposed to be hidden behind the first matching circuit 21a.

In the first and second embodiments, when viewed from the front, centers of the respective matching circuits 21 are disposed in substantially the same positions as centers of the transducers 10 to which the matching circuits 21 are respectively connected. However, in the present embodiment, when viewed from the front, the centers of the respective matching circuits 21 are offset in the array direction (the X-axis direction) with respect to the centers of the transducers 10 to which the matching circuits 21 are respectively connected.

By allocating the plurality of matching circuits 21 to the upper layer 20a and the lower layer 20b, distances to which from the array surface 13 are different, in this way, an inter-center distance of an array of the matching circuits 21 viewed from the direction orthogonal to the array surface 13 can be set shorter than an external shape of the matching circuit 21. Consequently, an inter-center distance of an array of the transducers 10 can be reduced without being affected by an external shape dimension of the matching circuit 21.

In the present embodiment, as in the first and second embodiments, concerning at least one of the wiring sections, the matching circuits, and the cables, by using the wiring section, the matching circuit, or the cable having different electric impedance, electric impedance for each of the transducers 10 between the plurality of transducers 10 and the driving apparatus is adjusted.

Therefore, in the present embodiment, when the connector section 4 is connected to the driving apparatus 5, it is possible to equally perform impedance matching between all the transducers 10 configuring the transducer array 11 and the driving apparatus 5. It is possible to improve efficiency of transmission of a signal.

As explained above, in the ultrasound observation apparatus 1 in the present embodiment, a reduction in size and improvement of resolution are realized by reducing the inter-center distance of the array of the transducers 10 in the transducer array 11 and improvement of sensitivity is realized by improving efficiency of transmission of a signal between the transducer 10 and the driving apparatus 5.

Fourth Embodiment

Figure 9:
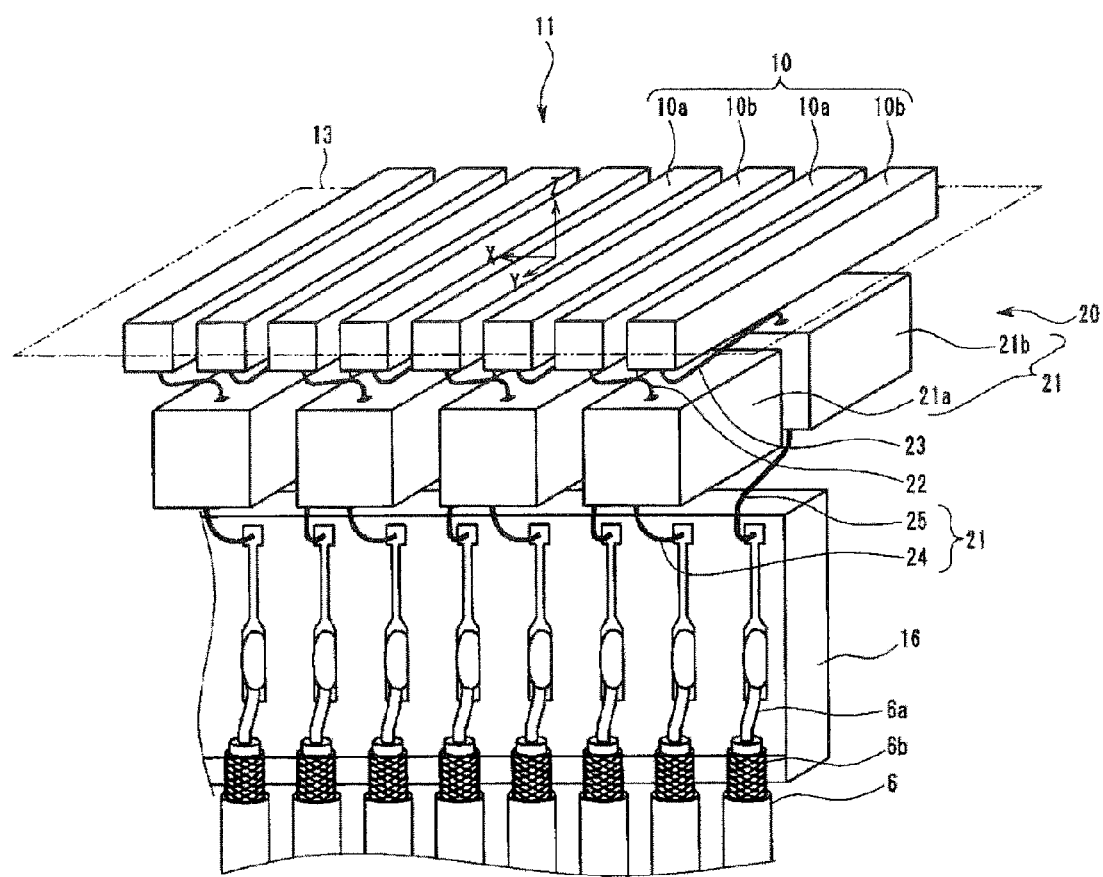
FIG. 9 is a perspective view for explaining disposition of transducers and matching circuits in an ultrasound transmitting/receiving section in a fourth embodiment.

A fourth embodiment of the present invention is explained below. In the following explanation, only differences from the first embodiment are explained. The same components as the components in the first embodiment are denoted by the same reference numerals and signs. Explanation of the components is omitted as appropriate. The ultrasound observation apparatus 1 in the present embodiment shown in FIG. 9 differs from the first to third embodiments in a form of an array of the plurality of matching circuits 21.

In the present embodiment, all of the plurality of matching circuits 21 are disposed at an equal distance from the array surface 13. The plurality of matching circuits 21 are arrayed to be allocated to a plurality of rows. In the present embodiment, as an example, the electric matching section 20 includes a first row and a second row, which are two rows divided in the direction (the Y-axis direction) orthogonal to the array direction. The plurality of matching circuits 21 are divided into a group consisting of the first matching circuits 21a disposed in the first row and a group consisting of the second matching circuits 21b disposed in the second row. The first matching circuit 21a and the second matching circuit 21b are arrayed at the same pitch in the X-axis direction.

The first matching circuit 21a and the second matching circuit 21b respectively connected to the first transducer 10a and the second transducer 10b, which are a pair of transducers adjacent to each other, are arrayed in the direction (the Y-axis direction) orthogonal to the array direction of the transducers 10 and are disposed in positions overlapping both of the first transducer 10a and the second transducer 10b when viewed from the front, which is the direction orthogonal to the array surface 13.

That is, in the present embodiment, a front end face of the first matching circuit 21a is opposed to rear end faces of both of the first transducer 10a and the second transducer 10b. A front end face of the second matching circuit 21b is also opposed to the rear end faces of both of the first transducer 10a and the second transducer 10b. In the present embodiment, when viewed from the front, the centers of the respective matching circuits 21 are offset in the array direction (the X-axis direction) and the direction (the Y-axis direction) orthogonal to the array direction with respect to the centers of the transducers 10 to which the matching circuits 21 are respectively connected.

In the present embodiment, by arraying the plurality of matching circuits 21 to be allocated to the plurality of rows, an inter-center distance of an array of the matching circuits 21 viewed from the direction orthogonal to the array surface 13 can be set shorter than an external shape of the matching circuit 21. Consequently, an inter-center distance of an array of the transducers 10 can be reduced without being affected by an external shape dimension of the matching circuit 21.

In the present embodiment, as in the first to third embodiments, concerning at least one of the wiring sections, the matching circuits, and the cables, by using the wiring section, the matching circuit, or the cable having different electric impedance, electric impedance for each of the transducers 10 between the plurality of transducers 10 and the driving apparatus is adjusted.

Therefore, in the present embodiment, when the connector section 4 is connected to the driving apparatus 5, it is possible to equally perform impedance matching between all the transducers 10 configuring the transducer array 11 and the driving apparatus 5. It is possible to improve efficiency of transmission of a signal.

As explained above, in the ultrasound observation apparatus 1 in the present embodiment, a reduction in size and improvement of resolution are realized by reducing the inter-center distance of the array of the transducers 10 in the transducer array 11 and improvement of sensitivity is realized by improving efficiency of transmission of a signal between the transducer 10 and the driving apparatus 5.

Note that the present invention is not limited to the embodiments explained above. The present invention can be changed as appropriate in a range not departing from the gist or the thought of the invention read from the claims and the entire specification. An ultrasound endoscope involving such a change is also included in the technical scope of the present invention.

What is claimed is:

1. An ultrasound endoscope including a cable for connecting the ultrasound endoscope to a driving apparatus, the ultrasound endoscope comprising:
    an insertion section insertable into a subject;
    a distal end portion located at a distal end of the insertion section and including a curved surface in at least a part of a cylindrical surface shape;
    a plurality of transducers provided at the distal end portion and arrayed in a surface shape on the curved surface to configure one array surface;
    an electrode formed in each of the transducers;
    a wiring section connected to the electrode to electrically connect the electrode and the cable; and
    matching circuits, at least one of which is provided at an end of or partway in the wiring section, provided with an electric circuit including a capacitor or an inductor, wherein
    the electrode, the wiring section, and the matching circuits are provided in each of the plurality of transducers, and, concerning at least one of the matching circuits, the matching circuit is disposed in the distal end portion such that relative positions of the matching circuit and a transducer to which the matching circuit is connected are different from relative positions of another matching circuit and another transducer to which the other matching circuit is connected, and
    the cable includes a core wire and an insulating layer enwrapping the core wire and functions as a matching section that matches electric impedance of each of the transducers between the plurality of transducers and the driving apparatus by varying a thickness or quality of material of the insulating layer, respectively.

2. The ultrasound endoscope according to claim 1, wherein, concerning at least one of the matching circuits, the matching circuit is disposed such that a distance between a center of the matching circuit and a center of a transducer to which the matching circuit is connected differs from a distance between a center of another matching circuit and a center of another transducer to which the other matching circuits are connected.

3. The ultrasound endoscope according to claim 1, wherein each of the transducer include a vibration surface, and a rear surface of the vibration surface and one surface of one of the matching circuits connected to another transducer is disposed to be at least partially opposed to each other.

4. The ultrasound endoscope according to claim 1, wherein each of the transducer include a vibration surface, and at least one of the plurality of matching circuits is disposed in a position where a center of the matching circuit is offset with respect to an orthogonal line from a center of a vibration surface of the transducer connected to the matching circuit.

5. The ultrasound endoscope according to claim 1, wherein at least one of the plurality of matching circuits has a characteristic different from a characteristic of another matching circuits.

6. The ultrasound endoscope according to claim 5, wherein each of the matching circuits differs according to a characteristic of each of the plurality of transducers connected to a corresponding one of the matching circuits.

7. The ultrasound endoscope according to claim 1, wherein all of the matching circuits have a same characteristic.

8. The ultrasound endoscope according to claim 7, wherein the matching circuits include a first matching circuit and a second matching circuit, the second matching circuit is provided farther than the first matching circuit with respect to the array surface, and a length of the wiring section for connecting the second matching circuit and the electrode is larger than a length of the wiring section for connecting the first matching circuit and the electrode.

9. The ultrasound endoscope according to claim 8, wherein at least a part of the second matching circuit is disposed to overlap the first matching circuit.

* * * * *